US011491096B2

(12) United States Patent
Turovets et al.

(10) Patent No.: US 11,491,096 B2
(45) Date of Patent: Nov. 8, 2022

(54) STEM CELL STIMULATING COMPOSITIONS AND METHODS

(71) Applicant: MEDICELL TECHNOLOGIES, LLC, Carlsbad, CA (US)

(72) Inventors: Nikolay Turovets, Carlsbad, CA (US); William B. Adams, Los Angeles, CA (US)

(73) Assignee: MEDICELL TECHNOLOGIES, LLC, Carlsbad, CA (US)

( * ) Notice: Subject to any disclaimer, the term of this patent is extended or adjusted under 35 U.S.C. 154(b) by 0 days.

(21) Appl. No.: 15/383,423

(22) Filed: Dec. 19, 2016

(65) Prior Publication Data

US 2017/0157015 A1   Jun. 8, 2017

Related U.S. Application Data

(60) Continuation of application No. PCT/US2015/036049, filed on Jun. 16, 2016, which
(Continued)

(51) Int. Cl.
*A61Q 19/10* (2006.01)
*A61Q 19/00* (2006.01)
(Continued)

(52) U.S. Cl.
CPC .................. *A61K 8/64* (2013.01); *A61Q 5/02* (2013.01); *A61Q 19/00* (2013.01); *A61Q 19/007* (2013.01);
(Continued)

(58) Field of Classification Search
CPC ...... A61Q 19/10; A61Q 19/08; A61Q 19/007; A61Q 5/02; A61Q 19/00; A61K 8/64; A61K 8/553; A61K 2800/74; A61K 8/14
See application file for complete search history.

(56) References Cited

U.S. PATENT DOCUMENTS 3,689,668 A * 9/1972 Piette ...................... A61K 8/44
424/582
5,242,902 A    9/1993 Murphy et al.
(Continued)

FOREIGN PATENT DOCUMENTS

WO        2014004339         1/2014

OTHER PUBLICATIONS

Ganceviciene et al.: Skin anti-aging strategies, Dermatoendocrinol. Jul. 1, 2012; 4(3): 308-319.*
(Continued)

*Primary Examiner* — Hong Yu
(74) *Attorney, Agent, or Firm* — Wilson Sonsini Goodrich & Rosati (57) ABSTRACT

The inventive subject is directed towards ready-to-use topical cosmetic formulations that include at least one defensin present in sub-antimicrobially effective concentrations. Surprisingly, even at such low concentrations, defensins recruit LGR6+ stem cells from hair follicles to the interfollicular space. Including defensins in the inventive topical cosmetic formulations may reduce one or more of wrinkle depth, wrinkle length, wrinkle width, pore size, irregularity in texture of a skin surface, oiliness, brown spots, and red spots in non-injured skin, thus reducing apparent age.

10 Claims, 2 Drawing Sheets

Related U.S. Application Data is a division of application No. 62/014,044, filed on Jun. 18, 2014.

(51) Int. Cl.

| | |
|---|---|
| *A61Q 5/02* | (2006.01) |
| *A61Q 19/08* | (2006.01) |
| *A61K 8/55* | (2006.01) |
| *A61K 8/64* | (2006.01) |
| *A61K 8/14* | (2006.01) |

(52) U.S. Cl.
CPC .............. *A61Q 19/08* (2013.01); *A61Q 19/10* (2013.01); *A61K 8/14* (2013.01); *A61K 8/553* (2013.01); *A61K 2800/74* (2013.01)

(56) References Cited

U.S. PATENT DOCUMENTS

| | | | |
|---|---|---|---|
| 6,329,340 B1 | 12/2001 | Bougueleret et al. | |
| 2008/0050398 A1* | 2/2008 | Bockmuehl | A61K 38/1709 424/190.1 |
| 2009/0048167 A1* | 2/2009 | Hillman | A61P 1/00 514/2.4 |
| 2013/0157964 A1* | 6/2013 | Selsted | A61K 38/10 514/21.1 |
| 2014/0127287 A1* | 5/2014 | Xiong | A61K 9/1271 424/450 |

OTHER PUBLICATIONS

Ericksen et al.: Antibacterial Activity and Specificity of the Six Human α-Defensins, Antimicrobial Agents and Chemotherapy, Jan. 2005, p. 269-275.*
Krishnakumari et al.: Antifungal Activities of Human Beta-Defensins HBD-1 to HBD-3 and Their C-Terminal Analogs Phd1 to Phd3, Antimicrobial Agents and Chemotherapy, Jan. 2009, p. 256-260.*
What causes our skin to age: retrieved from internet: https://www.aad.org/public/skin-hair-nails/anti-aging-skin-care/causes-of-aging-skin. Retrieved on Oct. 15, 2018.*
Sundaram et al.: Topically applied physiologically balanced growth factors: a new paradigm of skin rejuvenation, Journal of Drugs in Dermatology. May 2009;8(5 Suppl Skin Rejuenation):4-13.*
Huang et al.: In Vitro Activity of Human β-Defensin 2 against Pseudomonas aeruginosa in the Presence of Tear Fluid, Antimicrobial Agents and Chemotherapy, Nov. 2007, p. 3853-3860.*
Seo et al.: Interaction of Human β-Defensin 2 (HBD2) with Glycosaminoglycans, Biochemistry 2010, 49, 10486-10495, p. 10486.*
PCT Search Report & Written Opinion dated Oct. 19, 2015 for PCT/US2015/036049 filed Jun. 16, 2015 and entitled Stem Cell Compositions and Methods (29 pages).
Lough, D. et al., Stimulation of the follicular bulge LGR5+ and LGR6+ stem cells with the gut-derived human alpha defensin 5 results in decreased bacterial presence, enhanced wound healing, and hair growth from tissues devoid of adnexal structures, Plastic & Reconstructive Surgery Nov. 2013, vol. 132, No. 5, pp. 1159-1171.
Snippert, H. J. et al., Lgr6 marks stem cells in the hair follicle that generate all cell lineages of the skin, Science, Mar. 12, 2010, vol. 327, No. 5971, pp. 1385-1389.

EP Search Report (extended) dated Dec. 1, 2017 for EP Application 15810115.4 in the name of Medicell Technologies, LLC entitled Stem Cell Stimulating Compositions and Methods (7 pages).
Database GNPD (Online) Mintel: Jan. 1, 2014, Sepai Beauticeutical Division, V 3.0 Restart Serum. XP002755775; Database accession No. 2245082 (as cited in extended EP Search Report dated Dec. 1, 2017).
Database GNPD (Online) Mintel: Jul. 2, 2001, Jeanne Gitneau: "Protective Cream," XP002775776; Database accession No. 105830 (as cited in extended EP Search Report dated Dec. 1, 2017).
Joanna Baricelli et al., B-defensin-2 in Breast Milk Displays a Broad Antimicrobial Activity against Pathogenic Bacteria, J Pediatr (Rio J) 2015, 91(1), pp. 36-43.
"Salzman, et al., "Enteric defensins are essential regulators of intestinal microbial ecology" Nat immunol. 2010 11(1): 76-83".
"Baricelli, et al., "B-defensin-2 in breast milk displays a broad antimicrobial activity against pathogenic bacteria"j Pediatr (Rio J) 2015;91 (1): 36-43".
"Berens, et al., "Effect of Defensins-containing eye cream on periocular rhytids and skin quality" J Cosmet Dermaol. (2020)".
"Brogden, et al., "The emerging role of peptides and lipids as antimicrobial epidermal barriers and modulators of local inflammation" Skin Pharmacol Physiol. 2012;25(4): 167-181".
"Joly, et al. "human B-Defensins 2 and 3 Demonstrate Strain-Selective Activity against Oral microorganisms" Journal of Clinical microbiology (2004) vol. 42, No. 3, pp. 1024-1029".
"Lough, et al., "Stimulation of the Follicular Bulge LGR5+ and LGR6+ Stem Cells with the Gut-Derived human Alpha Defensin 5 Results in Decreased Bacterial presence, Enhanced Wound Healing, and Hair Growth from Tissues Devoid of Adnexal Structures" American Society of Plastics Surery (2013)".
"Midorikawa, et al., "*Staphylococcus aureus* Susceptibility to innate Antimicrobial peptides, B-Defensins ad CAP18, Expressed by Human Keratinocytes" Infection and Immunity, (2003) p. 3730-3739".
"Taub, et al., "Multi-Center , Double-blind, Vehicle-Controlled Clinical Trial of an Alpha and Beta Defensin-Containing Anti-Again Skin care Regimen with Clinical, Histopathologic, Immunohistochemical, Photographic, and Ultrasound Evaluation", Journal of Drugs in Dermatology, (2018) vol. 17 Issue 4".
"Wang, et al., "Antimicrobial Activity of human B-defensins Against Lactic Acid Bacteria" Nat Prod Res 2015;29(22):2164-2166".
"Yan, et al., "Synergistic Interactions between Mammalian Antimicrobial Defense Peptides" Antimicrobial Agents and Chemotherapy, (2001) p. 1558-1560".
Barnet: Roxisomes, Repairs DNA oxidative damage, 2 pages, 2008.
Plikus et al.: Epithelial stem cells and implications for wound repair. Semin Cell Dev Biol. 23(9):946-953 doi:10.1016/j.semcdb.2012.10.001 (2012).
Sederma: Matrixyl(R)synthe'6 TM: Synthesis of 6 Major Constituents of the Skin, 2 pages, Sep. 2010.
Sederma: Subliskin Tm Comfort Smoothness Reinforcement for thin and fragile skin, 2 pages, Oct. 2009.
Silab: Celldetox (R) A Powerful Biological Pathway for Skin Cell Detoxification and Longevity, 3 pages, 2009.
Silab: Cohesium (R) Lipids, Cohesion, Differentiation: The keys to successful hydration, 3 pages, 2008.
DSM Nutritional Products: Niacinamide PC Treasures to Discover, 3 pages, 2006.

* cited by examiner

Before treatment | After 6 weeks of treatment

STEM CELL STIMULATING COMPOSITIONS AND METHODS

INCORPORATION BY REFERENCE

This application is a continuation of International Application No. PCT/US2015/036049, filed Jul. 16, 2015 which claims priority to U.S. Provisional Application No. 62/014,044, which was filed Jun. 18, 2014, and which is incorporated by reference herein.

FIELD OF THE INVENTION

The field of the invention is topical cosmetic formulations using defensins to reduce the appearance of wrinkles, pores, irregularity in texture of a skin surface, oiliness, brown spots, and red spots in non-injured skin.

BACKGROUND

The following background discussion includes information that may be useful in understanding the present invention. It is not an admission that any of the information provided herein is prior art or relevant to the presently claimed invention, or that any publication specifically or implicitly referenced is prior art.

Since their initial discovery in the 1960's, there has been much research surrounding the role of defensins. Defensins are small cystein-rich proteins, usually only 14-85 amino acids long. Defensins can be found in invertebrates, vertebrates, and plants, and have been shown to be active against many bacteria, fungi, and viruses. In fact, much of the body of research has focused on the antimicrobial properties of defensins. However, in recent years, some research has explored other roles defensins may play in human skin, such as in wound healing or hair growth.

PCT Patent Application WO 2014/004339 A2 by Applicant ELC Management LLC teaches the use of a resveratrol-containing cosmetic composition to stimulate endogenous production of cellular beta defensins in skin cells. In order to illustrate this effect, the inventors tested the composition on Normal Human Epidermal Keratinocytes ("NHEK") in vitro and measured the presence of beta defensin in NHEK. The resulting stimulated quantities of defensin were very small (approximately 0.001 ng/ml). The inventors theorized that the stimulation of beta defensins in keratinocytes by resveratrol-containing compositions would be effective for treating acne, inhibiting microbial growth on the skin, and improving skin barrier repair. Because of the low stimulated quantities of beta defensin, and because the compositions do not actually contain defensins, it is questionable that these compositions would produce cosmetically meaningful results. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

On the other hand, defensins have been shown to play a significant role in wound healing. In the journal article titled "*Stimulation of the follicular bulge LGR5+ and LGR6+ stem cells with the gut-derived human alpha defensin 5 results in decreased bacterial presence, enhanced wound healing, and hair growth from tissues devoid of adnexal structures*" (Plast. Reconstr. Surg. 2013; 132(5):1159-71), Lough et al. report a human alpha defensin 5-containing formulation that was shown under experimental conditions to recruit LGR5+ and LGR6+ stem cells to third-degree burns in mice, which accelerated healing of the wound. However, these findings leave many questions. For example, in the experimental conditions described by Lough et al., it is unclear if LGR5+ and LGR6+ were activated by pro-inflammatory conditions and other factors already present in the wound or due to the topical application of defensins. Furthermore, the wound healing formulation used by Lough et al. contained concentrations of defensins at antimicrobially active concentrations (e.g. about $10^5$ ng/ml). However, this high concentration of defensin may make any resulting cosmetic composition more allergenic and more costly.

Therefore, even though defensin containing and defensin stimulating compositions are known, there is a need for a cosmetic topical formulation for use on healthy skin that makes use of defensins for reducing the visual appearance of age on the skin.

SUMMARY OF THE INVENTION

The inventive subject matter is directed towards various topical formulations, methods of manufacture of the topical formulation in which the topical formulation includes sub-antimicrobially effective concentrations of at least one defensin, and methods of applying the topical formulation to the healthy skin of users to reduce the apparent age of the users' skin.

In one aspect of the invention, a topical cosmetic formulation includes a defensin in a cosmetically acceptable carrier. Preferred topical cosmetic formulations are ready-to-use and contain the defensin at a sub-antimicrobially effective concentration, wherein the concentration is ineffective to inhibit growth of a microbial pathogen in a therapeutically effective manner. Still further preferred topical formulations may further comprise a blend of two or more different defensins, wherein the combined concentration of defensins in the formulation is a sub-antimicrobially effective concentration.

The inventors further contemplate methods of using defensins at sub-antimicrobially effective concentrations in topical formulations to recruit LGR6+ stem cells to an interfollicular space in non-injured skin. It should be appreciated that methods of recruiting LGR6+ stem cells may include a step of providing a topical formulation containing a sub-antimicrobial concentration of at least one defensin and a further step of applying the formulation to non-injured skin 1) to reduce at least one of wrinkle depth, wrinkle length, wrinkle width, pore size, irregularity in texture of a skin surface, oiliness, brown spots, and red spots 2) to improve skin brightness, 3) to lighten skin, and/or 4) to correct aging skin markers such as skin firmness, sagging contours, lines, wrinkles, enlarged pores, impurities, brightness or uneven skin tone, surface imperfections, evenness, overall clarity, age spots, hydration, dryness, smooth texture, radiance and redness in non-injured skin.

It is preferred that the inventive compositions, methods, and uses employ at least one of alpha-defensin 1, alpha-defensin 5, alpha-defensin 6, neutrophil defensin 1, neutrophil defensin 2, neutrophil defensin 3, neutrophil defensin 4, theta-defensin, beta-defensin 1, beta-defensin 2, beta-defensin 3, and beta-defensin 4. In especially preferred topical compositions and methods, alpha-defensin 5 and beta-defensin 3 are employed. It should be appreciated that the defensin may comprise a synthetic defensin, a human defensin, recombinant defensin, a monkey defensin, a mouse defensin, a rat defensin, a bovine defensin, a sheep defensin, a horse defensin, a rabbit defensin, a swine defensin, a dog defensin, and/or a cat defensin.

With respect to the sub-antimicrobially effective concentration of the first defensin in the ready-to-use topical cosmetic formulation, contemplated concentrations may be between 0.01 and 100 ng/ml, or between 1 and 30 ng/ml, including the end points of each range. Additionally, especially preferred embodiments of the inventive subject matter employ defensin concentrations of about 22 ng/ml and about 4.4 ng/ml in ready-to-use formulations.

The inventors unexpectedly found that, even at these low concentrations, defensins may be effective 1) to substantially reduce wrinkle depth, wrinkle length, wrinkle width, pore size, irregularity in texture of a skin surface, oiliness, brown spots, and red spots 2) to improve skin brightness, 3) to lighten skin, and/or 4) to correct aging skin markers such as skin firmness, sagging contours, lines, wrinkles, enlarged pores, impurities, brightness or uneven skin tone, surface imperfections, evenness, overall clarity, age spots, hydration, dryness, smooth texture, radiance and redness in non-injured skin. Without wishing to be bound by any particular theory, the effectiveness of defensins at these sub-antimicrobially effective concentrations may be due to the activation and/or recruitment of LGR6+ stem cells. Typically, defensins used in preferred embodiments of the inventive subject matter have a purity greater than 95% as shown by HPLC, and the sequence and proper disulfide bond formation of the defensins can be confirmed by tandem MS/MS.

Depending on the nature of the topical formulation, it should be recognized that defensins may be encapsulated in liposomes or other nanoparticles. In preferred formulations, defensins may also be associated with a carrier, in particular a protein carrier such as albumin (e.g., human serum albumin, bovine serum albumin, egg albumin, and recombinant albumin produced by rice, other plants, bacteria or yeast), also encapsulated in liposomes where desirable.

The inventors further contemplate that the topical cosmetic formulations may also include supplements to provide nutrition and support for LGR6+ stem cells. Typical supplements include human serum albumin, bovine serum albumin, egg albumin, recombinant albumin produced by rice, other plants, bacteria or yeast, plant hydrolysate, beta-cyclodextrin, glutamine, phospholipids, fibronectin, hyaluronate, hyaluronic acid, plant hydrolysate, L-alanyl-L-glutamine, gelatin, recombinant gelatin, Epidermal Growth Factor (EGF), vitamin E, Tocopheryl Nicotinate, and ubiquinone, coenzyme Q10, antioxidants.

The inventors have appreciated that the topical cosmetic formulations of the inventive subject matter can be included in kits with exfoliating masks. Especially preferred kits include a mask, a cream treatment formulation, and a serum treatment formulation.

Further aspects of the inventive subject matter provide methods of treating scars, sunburn, bruises, and other skin disorders in which the epidermal layers of the skin are largely intact. Exemplary methods include the steps of providing a topical formulation having at least one defensin at a sub-antimicrobially effective concentration and applying the formulation to non-injured skin under a protocol effective to substantially reduce the appearance of scars, sunburn, bruises, etc.

Various objects, features, aspects and advantages of the inventive subject matter will become more apparent from the following detailed description of preferred embodiments, along with the accompanying drawing figures in which like numerals represent like components.

DETAILED DESCRIPTION

The inventors unexpectedly discovered that sub-antimicrobial concentrations of defensins can achieve numerous desirable effects on non-injured skin when applied in ready-to-use topical formulations. Among other things, such topical formulations provided 1) significant reduction in wrinkles, pore size, irregularity in skin texture, oiliness, brown spots, and red spots, 2) improvement in skin brightness, 3) skin lightening, and/or 4) correction of aging skin markers such as skin firmness, sagging contours, lines, wrinkles, enlarged pores, impurities, brightness or uneven skin tone, surface imperfections, evenness, overall clarity, age spots, hydration, dryness, smooth texture, radiance and redness.

In one preferred embodiment, a ready-to-use topical cosmetic formulation comprises at least one defensin present in a topical cosmetic formulation at a sub-antimicrobially effective concentration. Of course it should be appreciated that topical formulations may contain one defensin, a combination of two defensins, or a combination of three or more defensins. The defensins used may be of the same or different types and subtypes. For example suitable defensins may include one or more of alpha-defensin 1, alpha-defensin 5, alpha-defensin 6, neutrophil defensin 1, neutrophil defensin 2, neutrophil defensin 3, neutrophil defensin 4, theta-defensin, beta-defensin 1, beta-defensin 2, beta-defensin 3, and beta-defensin 4. Especially preferred topical formulations contain alpha-defensin 5 and beta-defensin 3. When two more defensins are used in combination, each defensin may be present in equal quantities by mass or at mass ratios specified to achieve a desired result, such as 1:1.5, 1:2, 1:4, 1:5, etc. Notably, it should be appreciated that the total concentrations of defensins used in contemplated ready-to-use formulations are ineffective at inhibiting substantial proliferation of microbes in established skin infections in a therapeutically effective manner.

As used herein, the term "ready-to-use" indicates that the defensin-containing topical formulation is in a form that is presented for sale and application. It is contemplated that ready-to-use formulations can comprise a fully combined solution, cream, gel, serum, lotion, etc. Alternatively, the defensin can be packaged in a separate container (e.g., in a vial that pumps a defensin solution with a cream that the user blends before applying to unbroken skin) and combined with another topical formulation at the time of use/application.

As also used herein, the phrase "sub-antimicrobially effective concentration" means concentration(s) of defensins which are characterized by an inability to inhibit the proliferation of microbes in an established infection. Typically, ready-to-use topical formulations do not include concentrations greater than 1 µng/ml. In preferred embodiments, the concentration of defensins lies between 0.01 and 100 ng/ml, and even more typically between 1 and 30 ng/ml, wherein contemplated concentrations include the end points of each range. In even more preferred embodiments, the topical cosmetic formulations have defensin concentrations of about 22 ng/ml and 4.4 ng/ml. As used herein, when the term "about" is used in conjunction with a numeral, "about" means a range of plus or minus ten percent of the numerical value given, including end points. The recitation of ranges of values herein is merely intended to serve as a shorthand method of referring individually to each separate value falling within the range. Unless otherwise indicated herein, each individual value is incorporated into the specification as if it were individually recited herein.

General topical formulations may include any and all formulations suitable for cosmetic topical use, especially on non-injured skin. As used herein, the term "non-injured" skin refers to skin in which dermis and hypodermis are substantially intact. Therefore, viewed from a different perspective, non-injured skin will appear intact to the unaided eye, with no breach sufficiently large or deep to result in bleeding. Thus, non-injured (or "healthy") skin includes aged skin and skin with first degree sunburn, environmental exposure, bruising, or partially ablated stratum corneum. Non-injured (or healthy) skin also excludes skin displaying persistent infection with pathogens that result in visible symptoms and signs of infection.

With respect to the source of defensins, the inventors contemplate that defensins from both natural and synthetic sources may be suitable for incorporation into topical formulations. For example, defensins may be obtained from plants (e.g., *Arabidopsis*, pea, tobacco, and spruce), mammals, or other animals. Exemplary defensins derived from natural sources may include human defensins, monkey defensins, mouse defensins, rat defensins, bovine defensins, sheep defensins, horse defensins, rabbit defensins, swine defensins, dog defensins, and/or cat defensins.

Due to their relatively low quantities in a living organism and small molecular weight, it is generally preferred, however, that the defensins are synthetic defensins. Synthetic defensins include defensins produced by chemical synthesis (e.g., solid phase synthesis) or by recombinant technologies (e.g., produced by recombinant bacteria, yeast, tissue cultures, plants or animals). The inventors further contemplate that defensin analogues such as hapivirins and diprovirins may be used in some embodiments of the inventive subject matter. Still further, the inventors further contemplate that the defensins can also be modified to increase their activity and specificity for cosmetic improvements to the appearance of skin. For example, defensins may be unfolded and refolded under controlled conditions to ascertain proper disulfide bond formation (which can be monitored by MS analysis and/or CD spectroscopy). Alternatively, chemical modifications (e.g., using non-natural amino acids to increase half-life time, or derivatized proteinogenic amino acids to increase lipophilicity) are contemplated to tailor the defensins to a particular need.

Regardless of the source of the defensins, it should be appreciated that specific activity of defensins is dependent on various factors, including isomeric form and tertiary structure of the final protein. Thus, and especially where the defensin is synthetic, orthogonal protecting groups can be used to protect selected cysteine residues, which can then be individually deprotected and bonded with the matching target cysteine residue, leading to coordinated non-random disulfide bond formation. Use of such protecting groups in the synthetic strategy can give rise to defensins with a specific activity that is comparable to the specific activity of the native defensin. Any suitable characterization and quality control measures may be employed. Typically, the specific activity of defensins incorporated into the inventive topical formulations is measured by purity as determined by HPLC. In exemplary embodiments, the defensin is between 80% and 100% pure, more typically the defensin is at least 90% pure, or at least 95% pure, or at least 99% pure, or at least 99.9% pure. Additionally, proper amino acid sequence and disulfide bond formation can be confirmed by tandem MS/MS, for example.

With respect to suitable concentration of defensins in cosmetic formulations presented herein, it is contemplated that all concentrations are deemed appropriate so long as such concentrations are cosmetically effective (i.e., improves in the visual appearance of healthy skin, and especially 1) reduces wrinkles, pore size, irregularity in skin texture, oiliness, brown spots, and/or red spots, 2) improves skin brightness, 3) lightens skin, and/or 4) corrects aging skin markers such as skin firmness, sagging contours, lines, wrinkles, enlarged pores, impurities, brightness or uneven skin tone, surface imperfections, evenness, overall clarity, age spots, hydration, dryness, smooth texture, radiance and redness). Thus, it should be noted that the cosmetic formulation is intended to be used for improvement in visual appearance of healthy aged skin. In other words, the concentrations employed in the inventive subject matter are not intended to be therapies for the treatment of cuts, third degree burns, or other injuries where there is a loss of integrity in epidermis and dermal layers (typically associated with bleeding and/or scab formation). Consequently, the total concentration of defensins (single type or combination of distinct defensins) in the final cosmetic formulation as applied to the skin will be between 0.01 ng/ml and 100 ng/ml, or between 0.1 ng/ml and 100 ng/ml, or between 1 ng/ml and 100 ng/ml, or between 2 ng/ml and 80 ng/ml, or between 4 ng/ml and 60 ng/ml, or between 1 ng/ml and 30 ng/ml. Thus, preferred compositions include defensins at a concentration of at least 0.01 ng/ml, at least 0.1 ng/ml, at least 1 ng/ml, or at least 4 ng/ml, but no more than 200 ng/ml, no more than 100 ng/ml, no more than 75 ng/ml, or no more than 50 ng/ml.

In most instances the defensin is associated with a cosmetically acceptable protein to increase stability and/or delivery characteristics. In this context, it should be noted that the association is preferably non-covalent (e.g., electrostatic, ionic, hydrophobic, etc.), however, covalent attachment to a side group of the protein is not excluded. Exemplary proteins include lactoferrin, transferrin, and albumin (e.g., human serum albumin, bovine serum albumin, and egg albumin, recombinant albumin). The defensins and protein carriers may be in various ratios, including equimolar, sub-, and supramolar ratios. Additionally, combinations of two or more protein carriers may be used. For example, in a formulation in which two defensins are used, one defensin may be associated with one carrier, and the other defensin may be associated with a different carrier. Therefore, any combination of defensins and carriers are contemplated.

In still further contemplated aspects, the defensins (and carrier proteins) can be encapsulated in cosmetically acceptable formulations, and especially formulations using a lipid membrane. For example, liposomes, microcapsules, nanocapsules, microparticles, nanoparticles, microparticle delivery systems, are especially contemplated. A description of some cosmetically acceptable cosmetic delivery systems can be found in Maherani et al, "*Liposomes: A Review of Manufacturing Techniques and Targeting Strategy*," Current Nanoscience; 7:436-452 (2011). A preferred method of liposome manufacturing is shear method. Preferred cosmetic delivery systems resemble naturally occurring membranes, are flexible, and can penetrate interstitial spaces between cells. It is further contemplated that cosmetic delivery systems may have monolayer, bilayer (e.g. unilammellar vesicle or ULV), or multi layer structures (e.g. multilammerlar vesicle or MLV). Additionally, multilayer liposomes, microcapsules, microsomes, and nanaocapsules may have nested structures (e.g. multivesicular vesicle or MVV). Cosmetic delivery systems used in the topical formulations can range in size from 500 nm to 10 microns. In the preparation of cosmetic delivery systems, all cosmetically acceptable lipid compositions are contemplated, especially pharmaceutically acceptable lipids. In most instances preferred cosmetic delivery systems comprise amphipathic or amphiphilic molecules such as phospholipids or combinations of phospholipids (e.g., phosphatidylcholine, phosphatidylethanolamine, phosphatidic acid, phosphatidylserine, and phosphoinositides). Additionally, in some instances contemplated cosmetic delivery systems can contain additive(s) such as sterols, polyethylene glycol, cholesterol, dicethylphosphate, stearyl amine, etc. With respect to the amount of delivery systems incorporated in each ready-to-use formulation, the cosmetic delivery system content will typically be adjusted to achieve a sub-antimicrobial concentration of defensins within a preferred range. Unilamellar vesicles/liposomes can be produced using high shear techniques. These vesicles have a greater Zeta Potential than the typical liposome, which allows for smaller, more uniform particle size with increased stability. Zeta Potential is an indicator of the electronic charge on the surface of any macroscopic material that is in contact with a liquid. This can be used to predict and control the stability of suspensions; the higher the Zeta Potential, the greater the stability of the molecule because the charged particles are able to repel and overcome their innate affinity to assemble.

It should be noted that defensins, protein carriers, liposomes, or other membranaceous structures have a molecular weight that exceeds transmembrane delivery, and even delivery across the stratum corneum. Nevertheless, as is discussed in more detail, the defensins have a profound effect on stem cell activity in dermal and hypodermal layers. While not wishing to be bound by any theory or hypothesis, the inventors contemplate that the liposomal formulations have the ability to transport the defensins via an interstitial route and/or to invade the hair follicle to a depth and concentration sufficient to activate LGR6+ cells. Viewed from another perspective, the use of cosmetic delivery systems is thought to aid in the delivery of defensins as one would not expect defensins per se to penetrate the stratum corneum of the skin (acting as a barrier to molecules with molecular weights greater than 500 Da). Moreover, when associated with albumin (65-70 kDa) and/or liposomes, it becomes at least conceptually even more difficult for the defensin composition to penetrate unbroken skin. Thus, the inventors hypothesize that the mechanism for delivering defensins is different in unbroken skin when compared with broken or injured skin.

In another aspect, the inventors advantageously provide additional ingredients that nourish and support the recruited stem cells in healthy skin. For example, albumin (e.g., human serum albumin, bovine serum albumin), egg albumin (albumen), recombinant albumin, plant hydrolysate, and β-cyclodextrin, glutamine, phospholipids (liposomes), fibronectin, hyaluronate, plant hydrolysate, L-alanyl-L-glutamine, gelatin, Vitamin E (tocopheryl nicotinate), ubiquinone (coenzyme $Q_{10}$), gelatin, recombinant gelatin, hyaluronic acid, Epidermal Growth Factor can provide nutrition and support to the stem cells.

In yet further contemplated aspects, cosmetic treatment of healthy skin may further be assisted by supplemental procedures, and especially contemplated procedures include chemical and/or mechanical exfoliation. For example, chemical exfoliation may be performed using one or more proteases (for example papain, *Lactobacillus*/Pumpkin Ferment Extract, *Lactobacillus/Punica Granatum* Fruit Ferment Extract), alpha-hydroxy acids, etc. while mechanical exfoliation may be performed using sugar crystals, cellulosic plant matter, tape stripping, frozen $CO_2$, polymeric beads, and silica granules.

Based on the above and further data (not shown), the inventive subject matter is thus also directed to methods and use of sub-antimicrobially active concentrations of defensins in topical cosmetic formulations to recruit LGR6+ stem cells to the interfollicular space in non-injured skin. Most typically, a user will be instructed to apply the topical formulation to non-injured skin under a protocol effective 1) to reduce at least one of wrinkle depth, wrinkle length, wrinkle width, pore size, irregularity in texture of a skin surface, oiliness, brown spots, and red spots in non-injured skin, 2) to improve skin brightness, 3) to lighten skin, and/or 4) to correct aging skin markers such as skin firmness, sagging contours, lines, wrinkles, enlarged pores, impurities, brightness or uneven skin tone, surface imperfections, evenness, overall clarity, age spots, hydration, dryness, smooth texture, radiance and redness. For example, defensins will preferably be applied at least once daily (or twice daily) for a period of at least one week, or two weeks, three weeks, six weeks, or even longer. Beneficially, the total quantity of applied formulations is such that the formulation is absorbed into the skin. For example, topical formulations are typically applied at 0.1-500 mg per $cm^2$, 0.1-500 mg per $cm^2$, 0.5-300 mg per $cm^2$, 5-500 mg per $cm^2$, or 100-500 mg per $cm^2$.

Using the compositions presented herein, the inventors discovered that the cosmetic formulations that included the defensins 1) reduces at least one of wrinkle depth, wrinkle length, wrinkle width, pore size, irregularity in texture of a skin surface, oiliness, brown spots, and red spots in non-injured skin, and/or 2) improves skin brightness, and/or 3) lightens skin, and/or 4) corrects at least one aging skin markers such as skin firmness, sagging contours, lines, wrinkles, enlarged pores, impurities, brightness or uneven skin tone, surface imperfections, evenness, overall clarity, age spots, hydration, dryness, smooth texture, radiance and redness. Furthermore, observed effects (data not shown) included treatment of a scar, such that the appearance of the scar is reduced after application of the topical formulation. The inventors contemplate that other non-wound conditions such as sunburn and discoloration may be treated according to the inventive uses and methods.

EXAMPLES

While the cosmetic formulations may be prepared using any number of ingredients and formulations known in the art, preferred topical formulations include those that are ready-to-use and can be applied by a user. Therefore, with respect to cosmetically acceptable carriers, all cosmetically acceptable carriers are contemplated and include creams, oil-in-water emulsions, water-in-oil emulsions, foams, mousses, ointments, lotions, suspensions, serum, gels, etc. Example Topical Cosmetic Cream Formulation Ingredient List:

Water (Aqua), *Carthamus Tinctorius* (Safflower) Oleosomes, *Butyrospermum Parkii* (Shea) Butter, *Macadamia Integrifolia* Seed Oil, Niacinamide, Yeast Extract, Ammonium Acryloyldimethyltaurate/VP Copolymer, *Helianthus Annuus* (Sunflower) Seed Oil, Phospholipids, Alpha-Defensin 5, Beta-Defensin 3, Hyaluronic Acid, *Ophiopogon Japonicus* Root Extract, Hydrolyzed *Candida Saitoana* Extract, Sea Whip Extract, *Lycium Chinense* Fruit Extract, *Vaccinium Angustifolium* Fruit Extract, *Vaccinium Marcrocarpon* Fruit (Cranberry) Fruit Extract, *Rosmarinus officinalis* (Rosemary) Leaf Extract, Panthenol, Albumin, Tocopheryl Acetate, Ubiquinone, L-Alanyl-L-Glutamine, Leuconostoc/Radish Root Ferment Filtrate, Gelatin, SH Oligopeptide-1, Xanthan Gum, Phytic Acid, Polysorbate 20, Caprylic/Capric Triglyceride, Phenoxyethanol, Caprylyl Glycol, Ethylhexylglycerin, Hexylene Glycol, Potassium Sorbate, Sodium Chloride, Fragrance.

Example Topical Cosmetic Serum Formulation Ingredient List:

Water (Aqua), Cyclopentasiloxane, Glycerin, Niacinamide, Sinorhizobium Meliloti Ferment Filtrate, Dimethicone, Polysorbate 20, Dimethicone/Vinyl Dimethicone Crosspolymer, Lauryl PEG-9 Polydimethylsiloxyethyl Dimethicone, Ammonium Acryloyldimethyltaurate/VP Copolymer, Phospholipids, Alpha-Defensin 5, Beta-Defensin 3, Palmitoyl Tripeptide-38, Sodium Hyaluronate, *Arabidopsis Thaliana* Extract, Sea Whip Extract, Ergothioneine, *Helianthus Annuus* (Sunflower) Seed Oil, *Rosmarinus Offinalis* (Rosemary) Leaf Extract, SH Oligopeptide-1, Tocopheryl Acetate, Ubiquinone, Leuconostoc/Radish Root Ferment Filtrate, Albumin, Gelatin, L-Alanyl-L-Glutamine, Caprylic/Capric Triglyceride, Cetyl Hydroxyethylcellulose, Lecithin, Hydroxypropyl Cyclodextrin, Phytic Acid, Phenoxyethanol, Caprylyl Glycol, Ethylhexylglycerin, Hexylene Glycol, Sodium Chloride.

Example Mask:

Butylene Glycol, PEG-8, Tapioca Starch, Sucrose, Titanium Dioxide, Hydroxyethyl Acrylate/Sodium Acryloyldimethyl Taurate Copolymer, Squalane, Polysorbate 60, *Carica Papaya* (Papaya) Fruit, Papain, *Aloe Barbadensis* Leaf Juice, *Lactobacillus*/Pumpkin Ferment Extract, *Lactobacillus/Punica Granatum* Fruit Ferment Extract, Sea Whip Extract, *Cananga Odorata* Flower Oil, Citrus *Aurantium Dulcis* (Orange) Peel Oil, Caprylic/Capric Triglyceride, Lactic Acid, Phenoxyethanol, Caprylyl Glycol, Ethylhexylglycerin, Hexylene Glycol.

Example Liposome Formulation:

Table 1 below shows an exemplary cosmetic delivery liposome formulation including two types of defensins. These liposomes are typically incorporated into a cosmetic formulation at a fraction of about 1.0 wt % to 10.0 wt % for most skin care applications.

TABLE 1

Exemplary Liposome Formulation

| Component | Concentration |
| --- | --- |
| Water (protease-free) | to 100% |
| Albumin | 0.1-1.0 mg/ml |
| L-alanyl-L-glutamine | 0.1-1.0 mg/ml |
| Gelatin | 2-200 µg/ml |
| Matrix proteins | 1-100 ng/ml |
| Human alpha-defensin 5 | 1-200 ng/ml |
| Human beta-defensin 3 | 1-200 ng/ml |
| Growth factors (e.g., EGF, FGF-2) | 0.1-100 ng/ml |
| Phospholipids | 2-20 wt % |
| Antioxidants | 0.3-3 wt % |

In yet a further aspect of the inventive subject matter, topical cosmetic formulations can be offered together as a kit. Preferred kits include a mask formulation and a defensin-containing cream or serum treatment formulation. Even more preferred kits include a mask formulation and both the defensin-containing cream and serum treatment formulations.

In the manufacture of cosmetic defensin formulations, it is contemplated that concentrated defensin preparations can be added to cosmetic base formulations such that the concentration of the defensin in the ready-to-use product is at a targeted sub-antimicrobially effective concentration. Depending on the desired formulation, defensins can be incorporated into concentrated preparations as solutions, associated with carrier proteins, and more typically as liposomal formulations. Such concentrated defensin preparations can be added to the cosmetic base formulations in proportions as given below:

| Body Lotion (Oil-in-water) | | |
| --- | --- | --- |
| a) | PEG-7 hydrogenated castor oil | 2.00% |
| | PEG-20 glyceryl laurate | 1.00% |
| | cocoglycerides | 3.00% |
| | cetearyl alcohol | 1.00% |
| | cetearyl isononanoate | 4.00% |
| | octyl stearate | 4.00% |
| | phenoxyethanol, methylparaben, ethylparaben, butylparaben, propylparaben, isobutylparaben | 0.30% |
| b) | water, distilled | 73.40% |
| | phenoxyethanol, methylparaben, ethylparaben, butylparaben, propylparaben, isobutylparaben, glycerin | 0.30% |
| | glycerin | 3.00% |
| c) | Concentrated defensin preparation | 5.00% |
| d) | acrylamides copolymer, mineral oil, C13-C14 isoparaffin, polysorbate 85 | 3.00% |

Mixture a) is melted at approximately 70° C. and mixture b) is heated to approximately 70° C. and added to mixture a) while stirring. Stirring is continued until the lotion has cooled down to approximately 30° C. Then c) and d) are added while stirring, and the lotion is homogenized.

| Gel-Lotion | | |
| --- | --- | --- |
| a) | acrylamides copolymer, mineral oil, C13-14 isoparaffin, polysorbate 85 | 5.00% |
| | myreth-3 myristate | 4.00% |
| b) | water, distilled | 85.00% |
| | phenoxyethanol (and) methylparaben (and) ethylparaben (and) butylparaben (and) propylparaben (and) isobutylparaben | 0.50% |
| | xanthan gum | 0.50% |
| c) | Concentrated defensin preparation | 5.00% |

Mixture a) is dissolved at approximately 50° C. Mixture b) is dispersed at room temperature and added to a) while stirring. Then, composition c) is added while stirring.

| Oil-in-water Cream | | |
| --- | --- | --- |
| a) | cetearyl alcohol (and) ceteareth-20 | 8.00% |
| | cocoglycerides | 2.00% |
| | cetearyl alcohol | 2.00% |
| | dicaprylyl ether | 8.00% |
| | oleyl erucate | 7.00% |
| | phenoxyethanol, methylparaben, ethylparaben, butylparaben, propylparaben, isobutylparaben | 0.30% |

| Oil-in-water Cream | | | |
|---|---|---|---|
| b) | water, distilled | 62.40% | |
| | phenoxyethanol, methylparaben, ethylparaben, butylparaben, propylparaben, isobutylparaben | 0.30% | |
| | glycerin | 5.00% | |
| c) | Concentrated defensin preparation | 5.00% | |

Mixture a) is melted at approximately 70° C. and mixture b) is heated to approximately 70° C. and added to mixture a) while stirring. Stirring is continued until the cream has cooled down to approximately 30° C. Then, composition c) is added while stirring and the cream is homogenized.

| Water-in-oil Cream | | |
|---|---|---|
| a) | diisostearoyl polyglyceryl-3 dimer dilinoleate | 3.00% |
| | beeswax | 0.60% |
| | castor oil, hydrated | 0.40% |
| | paraffinum subliquidum | 5.00% |
| | isohexadecane | 10.00% |
| | PPG-15 stearyl ether | 2.00% |
| | dimethicone | 0.50% |
| | phenoxyethanol, methylparaben, ethylparaben, butylparaben, propylparaben, isobutyparaben | 0.30% |
| b) | water, distilled | 68.40% |
| | phenoxyethanol, methylparaben, ethylparaben, butylparaben, propylparaben, isobutylparaben | 0.30% |
| | glycerin | 3.00% |
| | $MgSO_4 \cdot 7H_2O$ | 1.00% |
| c) | Concentrated defensin preparation | 5.00% |
| d) | silica dimethyl silylate | 0.50% |

Mixture a) is heated to approximately 80° C., mixture b) is brought to 80° C. and added to a) while stirring. Stirring is continued until the cream has cooled down to approximately 30° C., then c) and d) are added, and the cream is homogenized.

| Shampoo | |
|---|---|
| Sodium polyoxyethylene lauryl ether sulfate | 15.0% |
| Alkyl polyglucoside | 4.0% |
| N-ethanol-N-methyl dodecanoic acid amide | 3.0% |
| EDTA-Na$_2$ | 0.3% |
| Malic acid to adjust pH to 6.0 | q.s. |
| Preservative | 0.5% |
| Concentrated defensin preparation | 10.0% |
| Purified water | balance |
| Total | 100.0% |

All ingredients are mixed together and the volume is brought to about 90 ml. The pH is then adjusted and the volume is finally adjusted to 100 ml (all percentages are weight %).

| Body Wash | |
|---|---|
| Sodium polyoxyethylene lauryl ether sulfate | 16.0% |
| Sodium polyoxyethylene | 5.0% |
| N-ethanol-N-methyl palm kernel oil fatty acid amide | 2.5% |
| Glycerin | 3.0% |
| Cationized cellulose | 0.1% |
| Ethylene glycol distearate | 3.0% |
| EDTA-Na$_2$ | 0.3% |
| Citric acid to adjust pH to 5.7 | q.s. |
| Preservative | 0.5% |
| Concentrated defensin preparation | 7.5% |
| Purified water | balance |
| Total | 100.0 |

All ingredients are mixed together and the volume is brought to about 90 ml. The pH is then adjusted and the volume is finally adjusted to 100 ml (all percentages are weight %).

| Face Wash | |
|---|---|
| Sodium polyoxyethylene lauryl ether sulfate | 20.0% |
| N-ethanol-N-methyl dodecanoic acid amide | 4.8% |
| Glycerin | 3.0% |
| Hydroxyethyl cellulose | 0.3% |
| Ethylene glycol distearate | 1.5% |
| EDTA-Na$_2$ | 0.3% |
| Citric acid to adjust pH to 6.0 | q.s. |
| Preservative | 0.5% |
| Concentrated defensin preparation | 10.0% |
| Purified water | balance |
| Total | 100.0 |

All ingredients are mixed together and the volume is brought to about 90 ml. The pH is then adjusted and the volume is finally adjusted to 100 ml (all percentages are weight %).

The inventors tested a preferred formulation of the inventive subject matter in two clinical studies, Clinical Study 1 and Clinical Study 2 (double-blinded study). Both studies were performed under the supervision of Dr. Gregory Keller, M.D, F.A.C.S at the Plastic Surgery Clinic in Santa Barbara, Calif. The design for both studies was substantially similar. Both clinical studies examined 10 subjects over a duration of 6 weeks. Each subject was given a cream, a serum, and a masque. Half of the subjects (Study 2) were given formulations of the cream, serum, and masques containing defensins. The other half of subjects were given placebo formulations of the cream, serum, and masque that were identical in composition to the test group, except the formulations did not contain defensins.

The inventors measured individual skin health scores for each participant before and after treatment using the QuantifiCare™ 3D LifeViz™ Imaging Clinical System and protocol developed by QuantifiCare Inc. (www.quantificare.com). The faces of each participants were scanned using the 3D LifeViz™ system and given a value for each the following categories: wrinkle depth, length, and width; pore depth; skin evenness; skin oiliness; skin brown spots; and skin red spots. The resulting values for each participant were then compared against a population with the same gender, age, and skin type, using QuantifiCare's Reference Population Database. The resulting skin heath score for each participant was a percentile ranking of skin health when compared with a population of people with the same age, gender, and skin type.

For example, Table 2 (below) shows the average age of each study group when compared to a population with corresponding age, gender, and skin type. Age was calculated using the wrinkle parameter, which is a combination of depth, length, and width of wrinkles in the forehead and cheeks.

TABLE 2

Average Age Ranking For Clinical Study 2 Before and After Treatment

| Group | Average Age Ranking | |
|---|---|---|
| | Before Treatment | After 6 Weeks |
| Placebo | 77% | 74% |
| Test Group | 61% | 81% |

Figure 1:
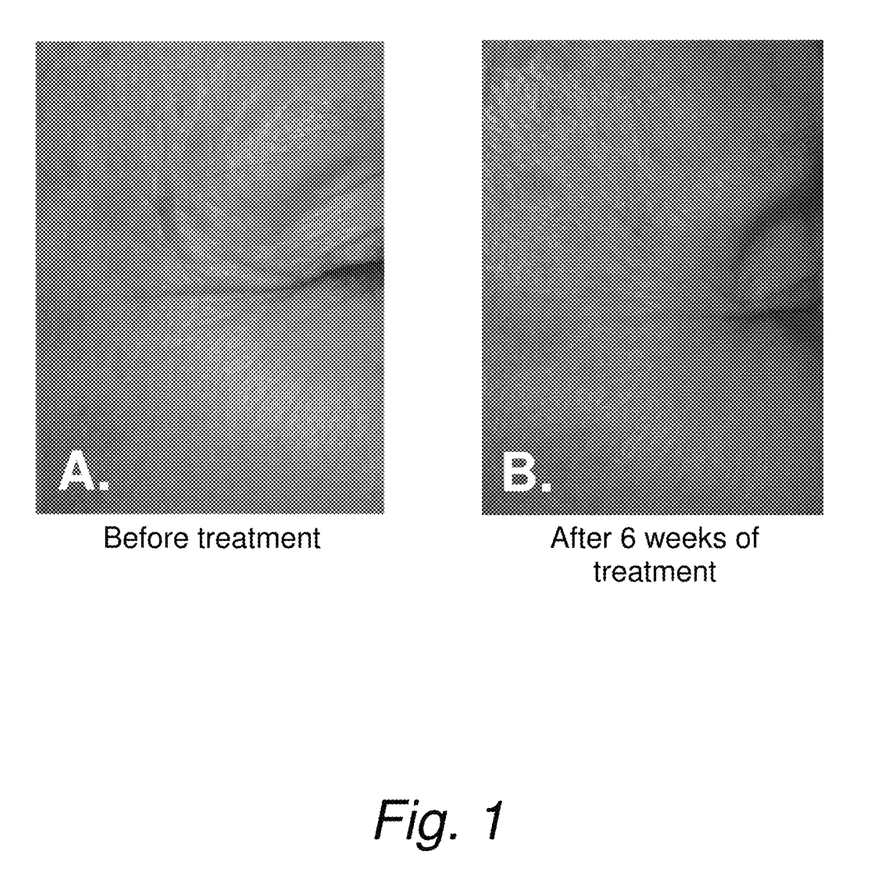
FIG. 1 shows side-by-side photographs that show reduction in wrinkles.

FIG. 1 shows the before (A) and after (B) images acquired by a 3D LifeViz™ system for participant 3-PC (63 year old female) of Clinical Study 1. Participant 3-PC was given the test formulation. Measurements by the 3D LifeViz™ system showed that participant 3-PC saw a reducing in visible skin age estimation (based on the skin evenness value calculated by the 3D LifeViz™ system) from 64 years to 37 years. Photos have not been retouched.

Figure 2:
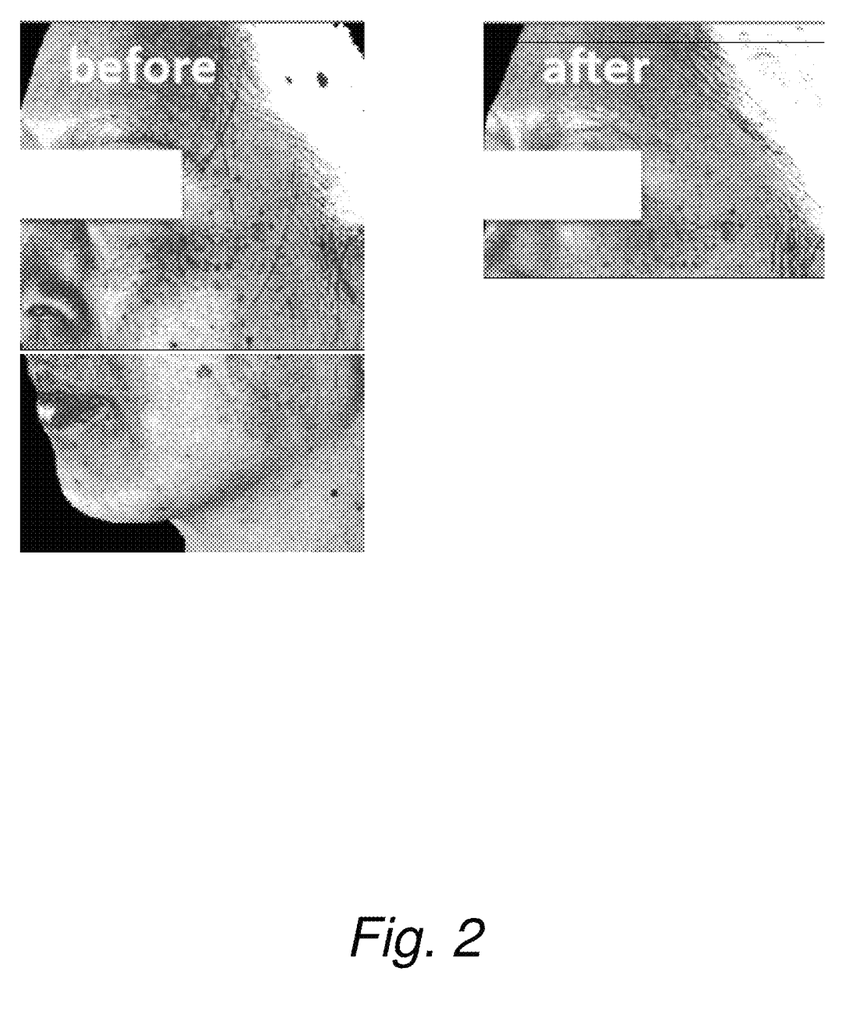
FIG. 2 shows side-by-side photographs that show a reduction in the appearance of brown spots.

FIG. 2 shows before (A) and after (B) images acquired by a 3D LifeViz™ system with the brown-spot filter for participant 8-IK (female) of Clinical Study 1. Participant 3-PC was given the test formulation. Images show a reduction in brown spots on the face as a result of treatment. Photos have not been retouched.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc. Moreover, as used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

What is claimed is:

1. A method of reducing pore size, reducing skin oiliness, or reducing appearance of brown spots in non-injured skin of an individual, comprising:
providing a topical formulation comprising alpha-defensin 5 and beta-defensin 3 at a concentration that is ineffective in inhibiting proliferation of a microbial pathogen, and that is effective to recruit LGR6+ stem cells to an interfollicular space in non-injured skin; and
applying the topical formulation to non-injured skin of the individual by topical application at least once daily for a period of one week or more to reduce an apparent age of the individual to thereby reduce pore size, reduce skin oiliness, or reduce appearance of brown or red spots in said non-injured skin of the individual.

2. The method of claim 1, wherein the topical formulation further comprises an additional defensin selected from the group consisting of alpha-defensin 1, alpha-defensin 6, neutrophil defensin 1, neutrophil defensin 2, neutrophil defensin 3, neutrophil defensin 4, theta-defensin, beta-defensin 1, and beta-defensin 4.

3. The method of claim 1, wherein each of the alpha-defensin 5 and beta-defensin 3 is provided in the topical formulation at 0.01 ng per mL to 100 ng per mL.

4. The method of claim 3, wherein each of the alpha-defensin 5 and beta-defensin 3 is provided in the topical formulation at 1 ng per mL to 30 ng per mL.

5. The method of claim 1, wherein the alpha-defensin 5 is provided in the topical formulation at 0.01 ng per mL to 100 ng per mL.

6. The method of claim 2, wherein the additional defensin is provided in the topical formulation at 0.01 ng per mL to 100 ng per mL.

7. The method of claim 1, wherein the beta-defensin 3 is provided in the topical formulation at 0.01 ng per mL to 100 ng per mL.

8. The method of claim 1, wherein the topical formulation does not comprise beta-defensin 2.

9. The method of claim 1, wherein the alpha-defensin 5 is encapsulated in a liposome.

10. The method of claim 1, wherein the beta-defensin 3 is encapsulated in a liposome.

* * * * *